(12) United States Patent
Gibson et al.

(10) Patent No.: US 11,090,498 B2
(45) Date of Patent: *Aug. 17, 2021

(54) IMPLANT MAGNET SYSTEM

(71) Applicant: Cochlear Limited, Macquarie University (AU)

(72) Inventors: Peter Gibson, South Coogee (AU); Charles Roger Aaron Leigh, North Epping (AU); Frank Risi, Newtown (AU); David Walker, Lane Cove (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/085,780

(22) Filed: Oct. 30, 2020

(65) Prior Publication Data

US 2021/0046318 A1    Feb. 18, 2021

Related U.S. Application Data

(60) Continuation of application No. 16/046,635, filed on Jul. 26, 2018, which is a division of application No. 15/010,627, filed on Jan. 29, 2016, now Pat. No. 10,058,702, which is a continuation of application No. 14/866,156, filed on Sep. 25, 2015, now Pat. No. (Continued)

(30) Foreign Application Priority Data

Apr. 9, 2003   (AU) ................................ 2003901696

(51) Int. Cl.
| | | |
|---|---|---|
| *A61N 1/375* | (2006.01) | |
| *A61N 1/378* | (2006.01) | |
| *A61N 1/08*  | (2006.01) | |

(52) U.S. Cl.
CPC ............. *A61N 1/375* (2013.01); *A61N 1/08* (2013.01); *A61N 1/3787* (2013.01)

(58) Field of Classification Search
CPC ......... A61N 1/375; A61N 1/08; A61N 1/3787
See application file for complete search history.

(56) References Cited

U.S. PATENT DOCUMENTS 3,043,000 A   7/1962  Hatfield
3,487,403 A   12/1969 Pihl
(Continued)

FOREIGN PATENT DOCUMENTS

GB    414579 A     8/1934
GB    2266045 A    10/1993
(Continued)

OTHER PUBLICATIONS

Daniel Rutter, "Comparison: Lightwave 2000, 3000, 4000, Illuminator and Pocket-Bright, and Petzl Tikka" pp. 1-30, Feb. 14, 2002. http://www.dansdata.com/ledlights7.htm.

(Continued)

*Primary Examiner* — Eric D. Bertram
(74) *Attorney, Agent, or Firm* — Pilloff Passino & Cosenza LLP; Martin J. Cosenza

(57) ABSTRACT

A magnetic alignment system that can form part of a cochlear implant system. The magnetic alignment system prevents substantial movement of a magnet of an implanted component during an MRI procedure or allows for easy removal of the magnet to facilitate the MRI procedure.

23 Claims, 13 Drawing Sheets

Related U.S. Application Data 10,232,171, which is a continuation of application No. 13/596,912, filed on Aug. 28, 2012, now Pat. No. 9,144,676, which is a continuation of application No. 11/857,397, filed on Sep. 18, 2007, now Pat. No. 8,255,058, which is a continuation of application No. 10/820,444, filed on Apr. 8, 2004, now abandoned.

(56) References Cited

U.S. PATENT DOCUMENTS

| | | | |
|---|---|---|---|
| 3,573,812 A | 4/1971 | Pihl | |
| D227,118 S | 6/1973 | Muraoka | |
| 3,771,685 A | 11/1973 | Micallef | |
| 3,801,767 A | 4/1974 | Marks | |
| 3,987,967 A | 10/1976 | Kuznetsov et al. | |
| 4,003,521 A | 1/1977 | Hess | |
| 4,038,990 A | 8/1977 | Thompson | |
| 4,197,840 A | 4/1980 | Beck et al. | |
| 4,199,741 A | 4/1980 | Paulet | |
| 4,226,164 A | 10/1980 | Carter | |
| 4,240,428 A | 12/1980 | Akhavi | |
| 4,257,936 A | 3/1981 | Matsumoto et al. | |
| 4,317,969 A | 3/1982 | Riegler et al. | |
| D267,541 S | 1/1983 | Kanemitsu | |
| 4,414,701 A | 11/1983 | Johnson | |
| 4,596,971 A | 6/1986 | Hirabayashi et al. | |
| 4,606,329 A | 8/1986 | Hough | |
| 4,610,621 A | 9/1986 | Taber et al. | |
| 4,628,907 A | 12/1986 | Epley | |
| 4,676,772 A | 6/1987 | Hooven | |
| 4,696,287 A | 9/1987 | Hortmann et al. | |
| 4,726,378 A | 2/1988 | Kaplan | |
| 4,731,718 A | 3/1988 | Sheu | |
| 4,736,747 A | 4/1988 | Drake | |
| RE32,947 E | 6/1989 | Dormer et al. | |
| 4,868,530 A | 9/1989 | Ahs | |
| 4,917,504 A | 4/1990 | Scott et al. | |
| 4,918,745 A | 4/1990 | Hutchison | |
| 4,920,679 A | 5/1990 | Sarles et al. | |
| 5,014,592 A | 5/1991 | Zweig et al. | |
| 5,015,224 A | 5/1991 | Maniglia | |
| 5,096,763 A | 3/1992 | Ogata et al. | |
| 5,105,811 A | 4/1992 | Kuzma | |
| 5,183,056 A | 2/1993 | Dalen et al. | |
| 5,196,710 A | 3/1993 | Kalfaian | |
| 5,314,453 A | 5/1994 | Jeutter | |
| D348,067 S | 6/1994 | Lucey et al. | |
| 5,456,654 A | 10/1995 | Ball | |
| 5,549,658 A | 8/1996 | Shannon et al. | |
| 5,554,096 A | 9/1996 | Ball | |
| 5,603,726 A | 2/1997 | Schulman et al. | |
| 5,624,376 A | 4/1997 | Ball et al. | |
| 5,630,835 A | 5/1997 | Brownlee | |
| 5,716,407 A | 2/1998 | Knapp et al. | |
| 5,749,912 A | 5/1998 | Zhang et al. | |
| 5,775,652 A | 7/1998 | Crawshaw et al. | |
| 5,785,477 A | 7/1998 | McGuffey et al. | |
| 5,800,336 A | 9/1998 | Ball et al. | |
| 5,857,958 A | 1/1999 | Ball et al. | |
| 5,877,664 A | 3/1999 | Jackson, Jr. | |
| 5,897,486 A | 4/1999 | Ball et al. | |
| 5,906,635 A | 5/1999 | Maniglia | |
| 5,913,815 A | 6/1999 | Ball et al. | |
| 5,971,334 A | 10/1999 | Crawshaw et al. | |
| 6,011,993 A | 1/2000 | Tziviskos et al. | |
| 6,040,762 A | 3/2000 | Tompkins | |
| 6,073,973 A | 6/2000 | Boscaljon et al. | |
| 6,138,681 A | 10/2000 | Chen et al. | |
| 6,157,278 A | 12/2000 | Katznelson et al. | |
| 6,157,281 A | 12/2000 | Katznelson et al. | |
| 6,171,229 B1 | 1/2001 | Kroll et al. | |
| 6,175,767 B1 | 1/2001 | Doyle, Sr. | |
| 6,178,079 B1 | 1/2001 | Renger | |
| 6,178,353 B1 | 1/2001 | Griffith et al. | |
| 6,190,305 B1 | 2/2001 | Ball et al. | |
| 6,208,235 B1 | 3/2001 | Trontelj | |
| 6,208,882 B1 | 3/2001 | Lenarz et al. | |
| 6,217,508 B1 | 4/2001 | Ball et al. | |
| 6,219,580 B1 | 4/2001 | Faltys et al. | |
| 6,244,142 B1 | 6/2001 | Swanson | |
| 6,259,951 B1 | 7/2001 | Kuzma et al. | |
| 6,263,230 B1 | 7/2001 | Haynor et al. | |
| 6,272,382 B1 | 8/2001 | Faltys et al. | |
| 6,275,736 B1 | 8/2001 | Kuzma et al. | |
| 6,292,678 B1 | 9/2001 | Hall et al. | |
| 6,295,472 B1 | 9/2001 | Rubinstein et al. | |
| 6,295,473 B1 | 9/2001 | Rosar | |
| 6,308,101 B1 * | 10/2001 | Faltys | A61N 1/375 607/57 |
| 6,313,551 B1 | 11/2001 | Hazelton | |
| 6,348,070 B1 | 2/2002 | Teissl et al. | |
| 6,358,281 B1 | 3/2002 | Berrang et al. | |
| 6,401,723 B1 | 6/2002 | Garibaldi et al. | |
| 6,475,134 B1 | 11/2002 | Ball et al. | |
| 6,505,062 B1 | 1/2003 | Ritter et al. | |
| 6,506,987 B1 | 1/2003 | Woods | |
| 6,522,909 B1 | 2/2003 | Garibaldi et al. | |
| 6,542,777 B1 | 4/2003 | Griffith et al. | |
| 6,571,676 B1 | 6/2003 | Folsom et al. | |
| 6,668,065 B2 | 12/2003 | Lee et al. | |
| 6,838,963 B2 | 1/2005 | Zimmerling et al. | |
| 6,857,612 B2 | 2/2005 | Goodbred | |
| D512,416 S | 12/2005 | Malaver | |
| 6,991,594 B2 | 1/2006 | Holcomb | |
| 7,054,691 B1 * | 5/2006 | Kuzma | H04R 25/606 607/36 |
| 7,091,806 B2 | 8/2006 | Zimmerling et al. | |
| 7,190,247 B2 | 3/2007 | Zimmerling | |
| 7,200,504 B1 | 4/2007 | Fister | |
| 7,225,028 B2 | 5/2007 | Della Santina et al. | |
| 7,231,252 B2 | 6/2007 | Duncan et al. | |
| 7,338,028 B2 | 3/2008 | Zimmerling et al. | |
| 7,566,296 B2 | 7/2009 | Zimmerling et al. | |
| 7,610,096 B2 | 10/2009 | McDonald, III | |
| 7,642,887 B2 | 1/2010 | Zimmerling | |
| 7,647,120 B2 | 1/2010 | Della Santina et al. | |
| 7,695,427 B2 | 4/2010 | Kugler et al. | |
| 7,856,986 B2 | 12/2010 | Darley | |
| 7,976,453 B2 | 7/2011 | Zimmerling et al. | |
| 7,991,477 B2 | 8/2011 | McDonald, III | |
| 8,013,699 B2 | 9/2011 | Zimmerling | |
| 8,118,725 B2 | 2/2012 | Zimmerling et al. | |
| 8,211,174 B2 | 7/2012 | Park et al. | |
| 8,255,058 B2 | 8/2012 | Gibson et al. | |
| 8,260,435 B2 | 9/2012 | Johnson et al. | |
| 8,270,647 B2 | 9/2012 | Crawford et al. | |
| 8,340,774 B2 | 12/2012 | Hochmair et al. | |
| 8,515,112 B2 | 8/2013 | Crawford et al. | |
| 8,515,544 B2 | 8/2013 | Daly et al. | |
| 8,532,783 B2 | 9/2013 | Zimmerling et al. | |
| 8,634,909 B2 | 1/2014 | Zimmerling et al. | |
| 8,734,475 B2 | 5/2014 | Ekvall et al. | |
| 8,744,106 B2 | 6/2014 | Ball | |
| 8,758,394 B2 | 6/2014 | Zimmerling et al. | |
| 8,768,480 B2 | 7/2014 | Charvin | |
| 8,897,475 B2 | 11/2014 | Ball et al. | |
| 8,983,102 B2 | 3/2015 | Crawford et al. | |
| 9,022,917 B2 | 5/2015 | Kasic et al. | |
| RE45,701 E | 9/2015 | Zimmerling et al. | |
| 9,144,676 B2 | 9/2015 | Gibson et al. | |
| 10,058,702 B2 * | 8/2018 | Gibson | A61N 1/3787 |
| 10,232,171 B2 * | 3/2019 | Gibson | A61N 1/3787 |
| 2001/0021805 A1 | 9/2001 | Blume et al. | |
| 2002/0032484 A1 | 3/2002 | Hyde, Jr. | |
| 2002/0076071 A1 * | 6/2002 | Single | H04R 25/606 381/312 |
| 2002/0099421 A1 | 7/2002 | Goldsmith et al. | |
| 2003/0120202 A1 | 6/2003 | Gordon | |
| 2003/0139782 A1 | 7/2003 | Duncan | |
| 2003/0171787 A1 | 9/2003 | Money et al. | |
| 2003/0181956 A1 | 9/2003 | Duncan et al. | |
| 2004/0012470 A1 | 1/2004 | Zimmerling et al. | |
| 2004/0059423 A1 | 3/2004 | Barnes et al. | |
| 2004/0167450 A1 | 8/2004 | Buckman et al. | |

(56) References Cited

U.S. PATENT DOCUMENTS

| | | |
|---|---|---|
| 2004/0260361 A1 | 12/2004 | Gibson |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2005/0159791 A1 | 7/2005 | Daly et al. |
| 2005/0171579 A1 | 8/2005 | Tasche et al. |
| 2006/0030905 A1 | 2/2006 | Malaver |
| 2006/0184212 A1 | 8/2006 | Faltys et al. |
| 2006/0244560 A1 | 11/2006 | Zimmerling et al. |
| 2007/0126540 A1 | 6/2007 | Zimmerling |
| 2007/0208403 A1 | 9/2007 | Della Santina et al. |
| 2008/0221641 A1 | 9/2008 | Hochmair |
| 2009/0069869 A1 | 3/2009 | Stouffer et al. |
| 2009/0287278 A1 | 11/2009 | Charvin |
| 2011/0004278 A1 | 1/2011 | Aghassian |
| 2011/0022120 A1 | 1/2011 | Ball et al. |
| 2011/0264172 A1 | 10/2011 | Zimmerling et al. |
| 2011/0295053 A1 | 12/2011 | Ball |
| 2012/0022616 A1 | 1/2012 | Garnham et al. |
| 2012/0022647 A1 | 1/2012 | Leigh et al. |
| 2012/0029267 A1 | 2/2012 | Ball |
| 2012/0172659 A1 | 7/2012 | Ball et al. |
| 2012/0238799 A1 | 9/2012 | Ball et al. |
| 2012/0296155 A1 | 11/2012 | Ball |
| 2012/0323066 A1 | 12/2012 | Cho et al. |
| 2012/0330378 A1 | 12/2012 | Crawford et al. |
| 2013/0046131 A1 | 2/2013 | Ball et al. |
| 2013/0046360 A1 | 2/2013 | Gibson et al. |
| 2013/0053874 A1 | 2/2013 | Ekvall et al. |
| 2013/0110198 A1 | 5/2013 | Stoffaneller |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121447 A1 | 5/2014 | Kasic et al. |
| 2014/0213139 A1 | 7/2014 | Ferguson |
| 2014/0275736 A1 | 9/2014 | Ruppersberg et al. |
| 2014/0302741 A1 | 10/2014 | Whittaker |
| 2014/0343626 A1 | 11/2014 | Thenuwara et al. |
| 2015/0087892 A1 | 3/2015 | Tourrel et al. |
| 2015/0157778 A1 | 6/2015 | Ishiyama et al. |
| 2016/0008596 A1 | 1/2016 | Gibson et al. |
| 2016/0144170 A1 | 5/2016 | Gibson et al. |
| 2016/0361537 A1 | 12/2016 | Leigh et al. |
| 2017/0312503 A1 | 11/2017 | Leigh et al. |

FOREIGN PATENT DOCUMENTS

| | | |
|---|---|---|
| WO | 02056637 A1 | 7/2002 |
| WO | 03092326 A1 | 11/2003 |

OTHER PUBLICATIONS

Med-El, "Magnetic Resonance Imaging (MRI)," believed to be available in Jan. 2016.

D. Cuda et al., "Focused tight dressing does not prevent cochlear implant magnet migration under 1.5 Tesla MRI," believed to be available in Jan. 2016.

\* cited by examiner

IMPLANT MAGNET SYSTEM

CROSS-REFERENCE TO RELATED APPLICATIONS

The present application is a Continuation application of U.S. patent application Ser. No. 16/046,635, filed Jul. 26, 2018, which is a Divisional application of U.S. patent application Ser. No. 15/010,627, filed Jan. 29, 2016, now U.S. Pat. No. 10,058,702, which is a Continuation application of U.S. patent application Ser. No. 14/866,156, filed Sep. 25, 2015, now U.S. Pat. No. 10,232,171, which is a Continuation application of U.S. patent application Ser. No. 13/596,912, filed Aug. 28, 2012, now U.S. Pat. No. 9,144,676, which is a Continuation application of U.S. patent application Ser. No. 11/857,397, filed Sep. 18, 2007, now U.S. Pat. No. 8,255,058, which is a Continuation application of U.S. patent application Ser. No. 10/820,444, filed Apr. 8, 2004, which claims priority to AU Application No. 2003901696, filed Apr. 9, 2003, the entire contents of these applications being hereby incorporated by reference herein in their entirety.

BACKGROUND

Field of the Invention

The present invention relates to a cochlear implant and in particular to an MRI-compatible implantable component of a cochlear implant.

Cochlear implant systems bypass the hair cells in the cochlea and directly deliver electrical stimulation to the auditory nerve fibres, thereby allowing the brain to perceive a hearing sensation resembling the natural hearing sensation normally delivered to the auditory nerve.

Typically, cochlear implant systems have consisted of essentially two components, an external component commonly referred to as a processor unit and an internal implanted component commonly referred to as a stimulator/receiver unit. Traditionally, both of these components have cooperated together to provide the sound sensation to a user.

The external component may consist of a microphone for detecting sounds, a speech processor that converts the detected sounds, particularly speech, into a coded signal, a power source such as a battery, and an external transmitter antenna.

The coded signal output by the speech processor is transmitted transcutaneously to the implanted stimulator/receiver unit that can be situated within a recess of the temporal bone of the implantee. This transcutaneous transmission occurs via the external transmitter antenna which is positioned to communicate with an implanted receiver antenna provided with the stimulator/receiver unit.

The implanted stimulator/receiver unit traditionally includes a receiver antenna that receives the coded signal and power from the external processor component, and a stimulator that processes the coded signal and outputs a stimulation signal to an intracochlear electrode assembly which applies the electrical stimulation directly to the auditory nerve producing a hearing sensation corresponding to the original detected sound.

The commonly accepted method of providing the implanted stimulator with power and information is to transmit RF-power via an inductively coupled antenna coil system. In such a system, the external transmitter coil is usually positioned on the side of an implantee's head directly facing the implanted coil of the stimulator/receiver unit to allow for the transmission of the coded sound signal and power from the speech processor to the implanted unit. Such transmitters usually have a coil formed by a small number of turns of a single or multi-strand wire and a magnet at or near the hub of the coil. The magnet holds the transmitter coil in place due to magnetic attraction with a magnet of the implanted unit.

The implanted magnet can pose problems for those cochlear implant implantees that may be required to undergo magnetic resonance imaging (MRI). In this regard, although studies have indicated that MRI presents no major risk to such implantees, the magnetic fields used in MRI procedures have been shown to exert a torque force on the implanted magnet. This torque force, if significantly large, such as may be the case if a high field strength MRI is undertaken, has the potential to cause undesirable consequences such as dislodgement of the magnet from its casing as well as discomfort to the implantee. There is also the potential for significant distortion of the image obtained by MRI due to the presence of the magnet in the implantee's head, which may significantly negate the usefulness of the process.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In a first aspect, there is provided a magnetic alignment system for a transcutaneous transmitter/receiver system, said magnetic alignment system comprising an external transmitter unit and an implantable receiver component, both the external transmitter unit and the implantable receiver component having a magnet positioned therein to allow transcutaneous alignment of said external transmitter unit and said implantable receiver component; [0012] the system being characterised in that an outer surface of the magnet, or a casing for the magnet, of the implantable receiver component has an engagement surface that is engageable with a complementary engagement surface formed in a mounting of the implantable receiver component.

In a second aspect, there is provided a magnetic alignment system for a transcutaneous transmitter/receiver system, said magnetic alignment system comprising an external transmitter unit and an implantable receiver component, both the external transmitter unit and the implantable receiver component having a magnet positioned therein to allow transcutaneous alignment of said external transmitter unit and said implantable receiver component; [0014] the system being characterised in that the magnet of the implantable receiver component is housable within a pocket formed in a suitable biocompatible flexible mounting, said pocket having a restricted opening formed therein through which the magnet is insertable but which is sized to retain the magnet within the pocket following insertion.

In a third aspect, there is provided a magnetic alignment system for a transcutaneous transmitter/receiver system, said magnetic alignment system comprising an external transmitter unit and an implantable receiver component, both the external transmitter unit and the implantable receiver component having a magnet positioned therein to allow transcutaneous alignment of said external transmitter unit and said implantable receiver component; [0016] the system being characterised in that the magnet of the implantable receiver component is housed within a suitable biocompatible flexible mounting, said mounting having one or more indicia thereon or therein that identify the location of the magnet within the mounting In a fourth aspect, there is provided a magnetic alignment system for a transcutaneous transmitter/receiver system, said magnetic alignment system comprising an external transmitter unit and an implantable receiver component, both the external transmitter unit and the implantable receiver component having a magnet positioned therein to allow transcutaneous alignment of said external transmitter unit and said implantable receiver component; [0018] the system being characterised in that the magnet is releasably held within the receiver component by one or more retaining devices.

In a fifth aspect, there is provided a magnetic alignment system for a transcutaneous transmitter/receiver system, said magnetic alignment system comprising an external transmitter unit and an implantable receiver component, both the external transmitter unit and the implantable receiver component having a magnet positioned therein to allow transcutaneous alignment of said external transmitter unit and said implantable receiver component; [0020] the system being characterised in that the magnet of the implantable receiver component is housed within a recess formed in a suitable biocompatible flexible mounting, said recess being locatable adjacent the skull of the implantee in use thereby ensuring the magnet is held in the recess between the receiver component and the skull of the implantee In a sixth aspect, there is provided a magnetic alignment system for a transcutaneous transmitter/receiver system, said magnetic alignment system comprising an external transmitter unit and an implantable receiver component, the external transmitter unit having a magnet positioned therein and the implantable receiver component having a magnetised insert positioned therein to allow transcutaneous alignment of said external transmitter unit and said implantable receiver component; [0022] the magnetised insert of the implantable receiver component having a first end and a second end and increasing in width away from said first end towards said second end, the first end being positionable closer to the skin of the implantee in use to ensure self-centering of the magnet of the external transmitter unit with the magnetised insert of the receiver component In a seventh aspect, there is provided a magnetic alignment system for a transcutaneous transmitter/receiver system, said magnetic alignment system comprising an external transmitter unit and an implantable receiver component, both the external transmitter unit and the implantable receiver component having a magnet positioned therein to allow transcutaneous alignment of said external transmitter unit and said implantable receiver component; [0024] the system being characterised in that the implantable receiver component is detachably connectable to an implantable tissue stimulator device.

In an eighth aspect, there is provided a cochlear implant system comprising an external transmitter unit positionable on the outside of an implantee's head and an implantable receiver component positionable subcutaneously, wherein said external transmitter unit and said implantable receiver component each comprise a magnet therein to hold the external transmitter unit substantially in transcutaneous alignment with the implantable receiver component; wherein an outer surface of the magnet, or a casing for the magnet, of the implantable receiver component has an engagement surface that is engageable with a complementary engagement surface formed in a mounting of the implantable receiver component.

In a ninth aspect, there is provided a cochlear implant system comprising an external transmitter unit positionable on the outside of an implantee's head and an implantable receiver component positionable subcutaneously, wherein said external transmitter unit and said implantable receiver component each comprise a magnet therein to hold the external transmitter unit substantially in transcutaneous alignment with the implantable receiver component and wherein the magnet of the implantable receiver component is housable within a pocket formed in a suitable biocompatible flexible mounting, said pocket having a restricted opening formed therein through which the magnet is insertable but which is sized to retain the magnet within the pocket following insertion.

In a tenth aspect, there is provided a cochlear implant system comprising an external transmitter unit positionable on the outside of an implantee's head and an implantable receiver component positionable subcutaneously, wherein said external transmitter unit and said implantable receiver component each comprise a magnet therein to hold the external transmitter unit substantially in transcutaneous alignment with the implantable receiver component; wherein the magnet of the implantable receiver component is housed within a suitable biocompatible flexible mounting, said mounting having one or more indicia thereon or therein that identify the location of the magnet within the mounting In an eleventh aspect, there is provided a cochlear implant system comprising an external transmitter unit positionable on the outside of an implantee's head and an implantable receiver component positionable subcutaneously, wherein said external transmitter unit and said implantable receiver component each comprise a magnet therein to hold the external transmitter unit substantially in transcutaneous alignment with the implantable receiver component; wherein the magnet is releasably held within the receiver component by one or more retaining devices.

In a twelfth aspect, there is provided a cochlear implant system comprising an external transmitter unit positionable on the outside of an implantee's head and an implantable receiver component positionable subcutaneously, wherein said external transmitter unit and said implantable receiver component each comprise a magnet therein to hold the external transmitter unit substantially in transcutaneous alignment with the implantable receiver component; wherein the magnet of the implantable receiver component is housed within a recess formed in a suitable biocompatible flexible mounting, said recess being locatable adjacent the skull of the implantee in use thereby ensuring the magnet is held in the recess between the receiver component and the skull of the implantee.

In a thirteenth aspect, there is provided a cochlear implant system comprising an external transmitter unit positionable on the outside of an implantee's head and an implantable receiver component positionable subcutaneously, wherein the external transmitter unit has a magnet positioned therein and the implantable receiver component has a magnetised insert positioned therein to allow transcutaneous alignment of said external transmitter unit and said implantable receiver component; [0031] the magnetised insert of the implantable receiver component having a first end and a second end and increasing in width away from said first end towards said second end, the first end being positionable closer to the skin of the implantee in use to ensure self-centering of the magnet of the external transmitter unit with the magnetised insert of the receiver component.

In a fourteenth aspect, there is provided a cochlear implant system comprising an external transmitter unit positionable on the outside of an implantee's head and an implantable receiver component positionable subcutaneously, wherein said external transmitter unit and said implantable receiver component each comprise a magnet therein to hold the external transmitter unit substantially in transcutaneous alignment with the implantable receiver component; the system being characterised in that the implantable receiver component is detachably connectable to an implantable cochlea stimulator device

BRIEF DESCRIPTION OF THE DRAWINGS

By way of example only, exemplary embodiments are now described with reference to the accompanying drawings, in which:

FIG. 7b depicts how the magnet can be removed from the receiver component shown in FIG. 7a;

DETAILED DESCRIPTION

Exemplary embodiments of a magnetic alignment system according to the present invention are generally depicted in the accompanying drawings as part of a cochlear implant system.

Figure 1:
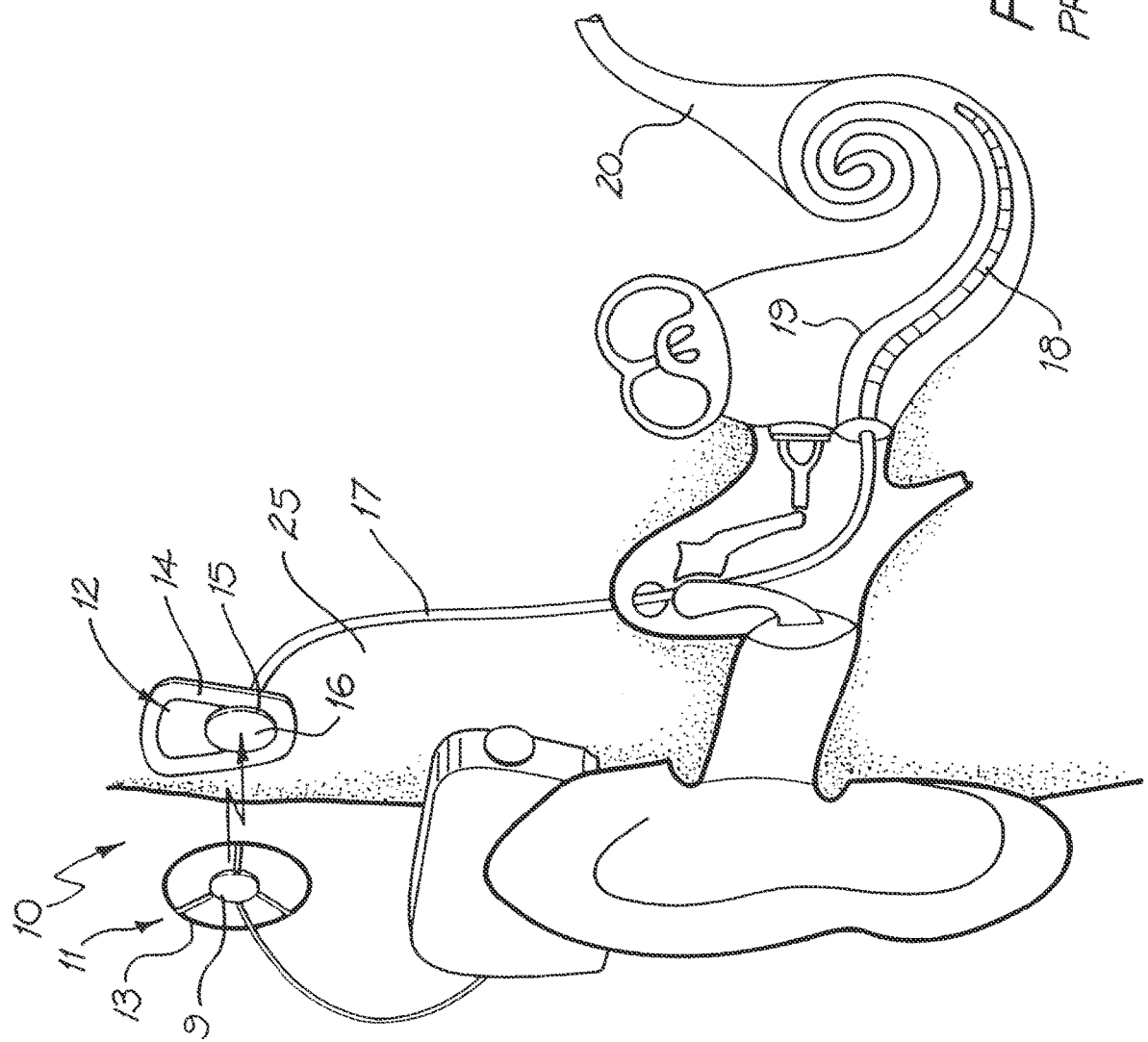
FIG. 1 is a pictorial representation of a cochlear implant system.

As depicted pictorially in FIG. 1, the magnetic alignment system 10 of a cochlear implant system comprises an external transmitter unit 11 and an implantable receiver component 12.

The external transmitter unit 11 comprises a transmitter antenna coil 13 which transmits coded signals to the implantable receiver component 12 via a radio frequency (RF) link.

The implantable receiver component 12 of the system comprises a receiver antenna coil 14 for receiving power and data from the transmitter coil 13 and a stimulator unit 15 within a housing 16. A cable 17 extends from the stimulator unit 15 to the cochlea and terminates in an electrode array 18. The signals received are applied by the array 18 to the basilar membrane 19 thereby stimulating the auditory nerve 20.

The receiver coil 14 typically comprises a wire antenna coil comprised of at least one and preferably two turns of electrically insulated platinum or gold wire.

The implantable receiver component 12 has a magnet to allow transcutaneous alignment of the external transmitter unit 11 (which also has a magnet 9) and the implantable receiver component 12.

The electrical insulation of the antenna coil is provided by a flexible silicone molding. In use, the implantable receiver component 12 can be positioned in a recess of the temporal bone adjacent the ear of an implantee.

Arrangements for preventing any or at least reducing substantial movement of the magnet of a transcutaneous transmitter/receiver system, such as a cochlear implant system, while a recipient is undergoing MRI scans of relatively low field strengths and arrangements that allow removal of the magnet from within the implantee if necessary, (such as when the recipient is to undergo MRI scans of relatively high field strengths) are depicted in the remaining drawings.

Figure 2A:
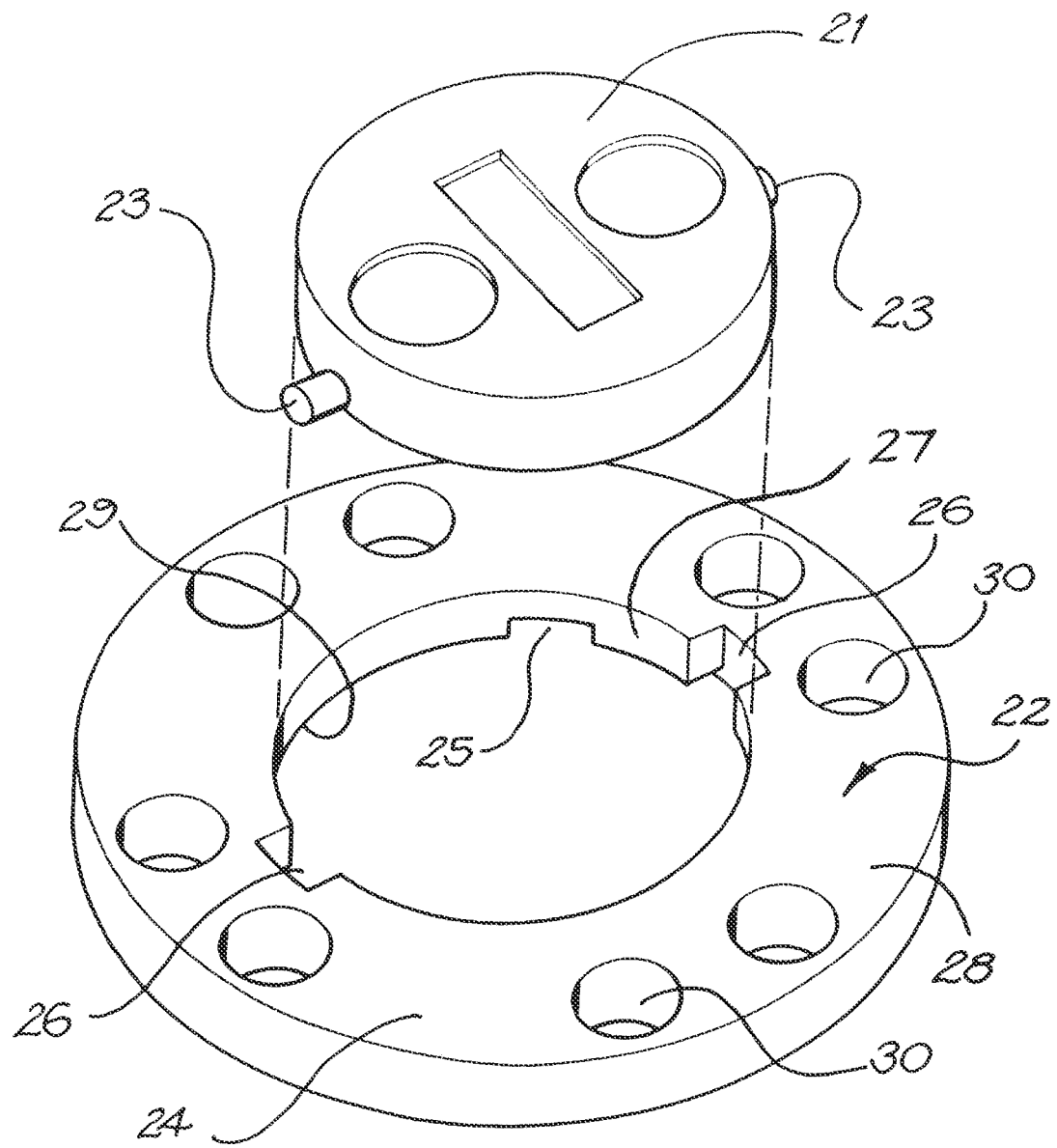
FIG. 2a is a schematic view of a magnet and mounting of one example of the invention.

In the embodiment depicted in FIG. 2a, the implantable receiver component of a cochlear implant system has a magnet 21 and a mounting 22. An outer surface of the magnet 21 has an engagement surface that is engageable with a complementary engagement surface formed in the mounting 22. The engagement between the magnet 21 and the mounting 22 minimises movement of the magnet, particularly when a patient undergoes an MRI procedure. Examples of the engagement surface and the complementary engagement surface are described in more detail below.

Figure 2:
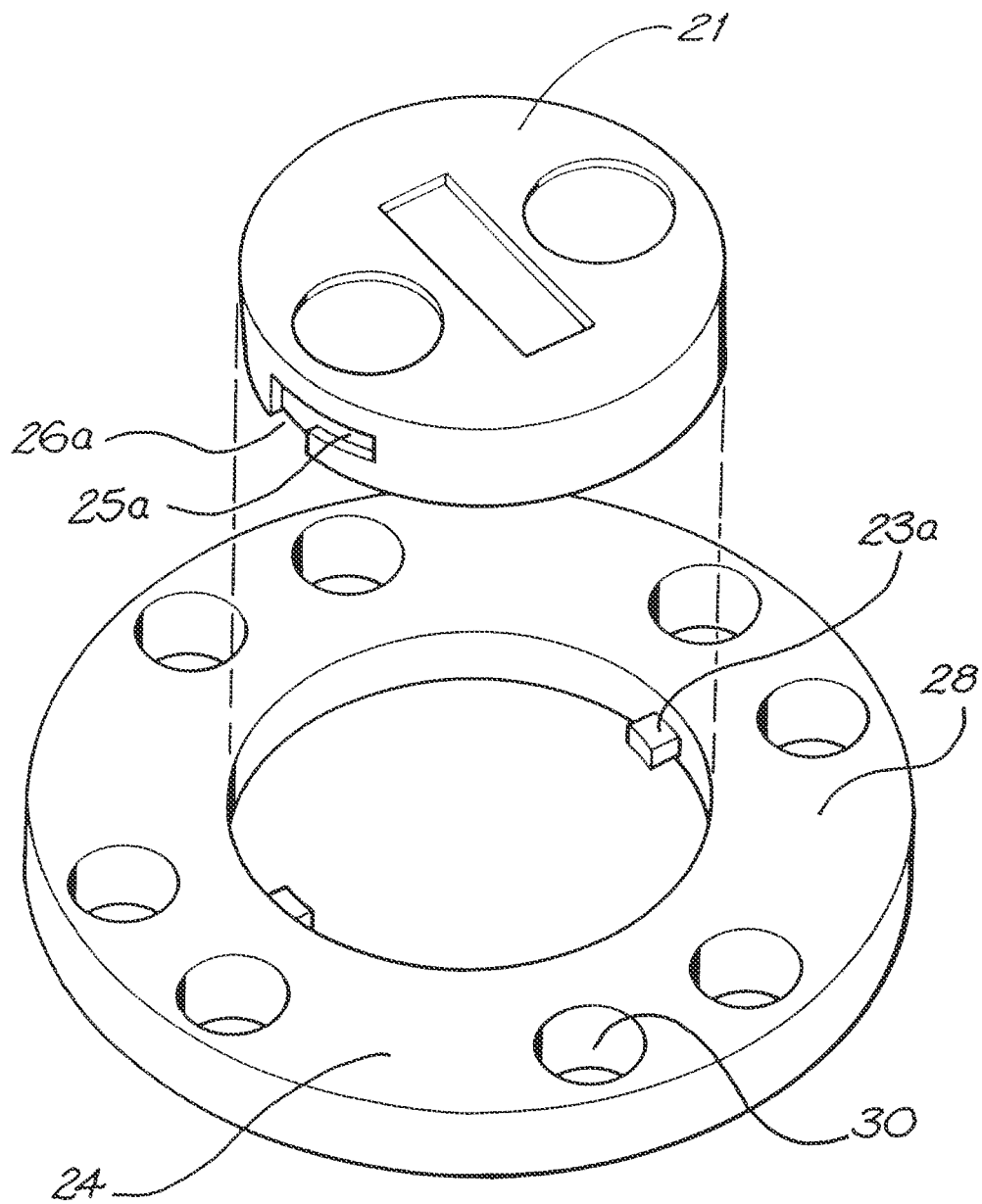
FIG. 2b depicts another arrangement for mounting the magnet in the receiver component.

In FIG. 2a, the magnet 21 has two extension members 23 that extend from opposite sides of the magnet. The magnet 21 may be received by the mounting 22 which is shown in FIG. 2 as a ring 24.

The ring 24 has at least one recessed portion 25. In an exemplary embodiment, the ring 24 includes two recessed portions 25 although in FIG. 2a, the second recessed portion is obscured from view. The recessed portions 25 receive the extension members 23 of the magnet 21 and hold the magnet in place within the ring 24.

The ring further includes two slots 26 in an inner surface 27 of the ring 24. The slots 26 extend from an upper surface 28 of the ring 24 to a lower surface 29 of the ring 24, i.e. through the thickness of the ring 24.

The magnet 21 may be relatively lowered into the center of the ring 24 such that the extension members 23 pass through slots 26. When moved beyond the lower surface 29 of the ring 24, the magnet is then rotatably moveable relative to the ring 24.

The magnet 21 may be rotated until the extension members align with the recessed portions 25.

The ring 24 may sit on, or at least partially within, a resilient silicone body of the implantable receiver component. To insert the magnet 21 into the center of the ring, a degree of force is therefore required to cause the extension member 23 to pass through the slots 26 and beyond the lower surface 29 of the ring 24. Once the magnet 21 is rotated and the extension members 23 are in alignment with the recessed portions 25, release of any force applied to the magnet 21 will result in the silicone body causing the extension members 23 to move up and away from the lower surface 29 of the ring and into the recessed portions 25. With the extension members 23 housed within the recessed portions 25, the magnet 21 is no longer rotatably moveable relative to the ring 24 (unless a degree of downward force is again applied to the magnet 21 to dislodge the extension members from the recessed portions).

The magnet 21 is, therefore, substantially but removably locked in place within the mounting 22.

Referring now to FIG. 2b, an alternative arrangement is shown in which the extension members 23a extend inwardly from the ring 24, and are arranged to engage with corresponding recessed portions 25a provided on the magnet 21. The number of slots 26a is shown as two, however, it is envisaged that one larger extension member 23a on the ring 24 could be used together with a corresponding single slot on the magnet 21.

Further, the ring 24 as shown in FIG. 2a has a series of holes 30 extending therethrough. The silicone of the implantable receiver component may extend through the holes 30 and provides a means of securing the ring 24 to the silicone body of the implantable receiver component. In this regard, portions of silicone may extend through the holes 30 and essentially act as rivets to mechanically lock the ring 24 in place. This added level of security may be desirable when the magnet is subjected to MRI and particularly to high field strengths.

In this aspect, the engagement surface of the magnet or the magnet casing can be a screw thread. The complementary engagement surface of the mounting can also be a screw thread that is formed in the mounting. In one embodiment, the mounting has a ring member mounted therein. The internal surface of the ring member may form the complementary engagement surface and may be a screw thread. The ring member can be made of a ceramic or plastics material. The mounting can be formed from a suitable biocompatible silicone.

Figure 3:
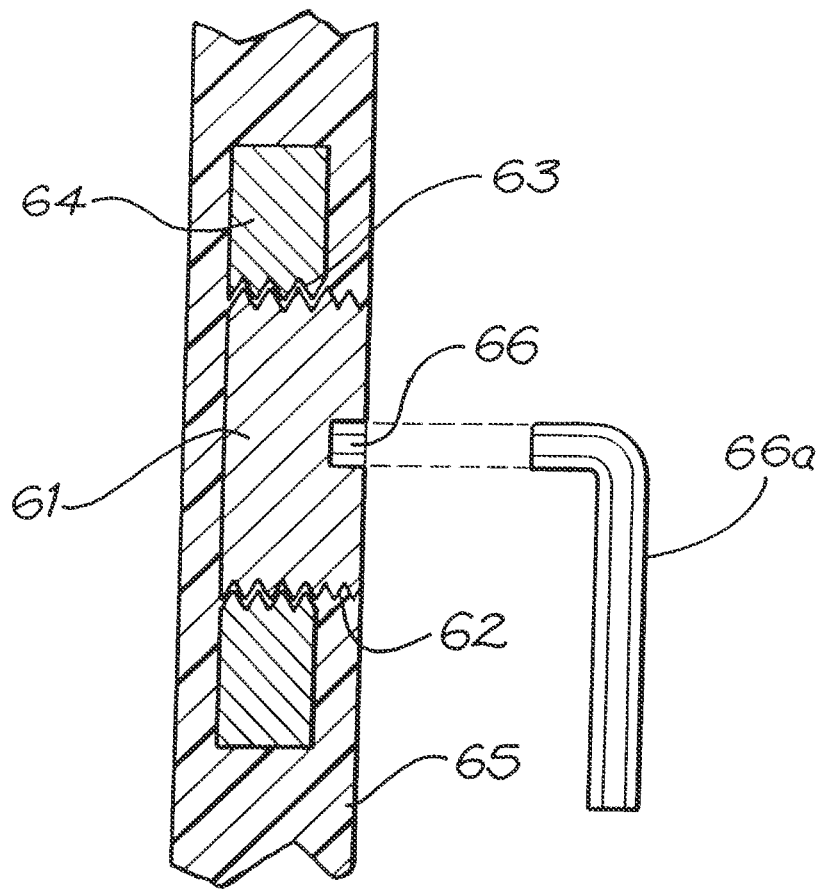
FIG. 3 depicts a still further arrangement for mounting the magnet in the receiver component.

As depicted in FIG. 3, the magnet can be screwed into or unscrewed from the mounting.

In FIG. 3, the outer surface of magnet 61 has a screw thread 62 formed therein. The screw thread 62 is engageable with a complementary thread 63 formed in a mounting ring 64 within the implantable component body (here depicted as 65). The mounting ring 64 can be made of a metal, ceramic or plastics material while the body 65 can be formed from a suitable biocompatible material, such as silicone.

As depicted, a top surface of the magnet 61 can have a slot 66 formed therein that can receive a tool, such as an allen key 66a as shown, or a screwdriver or the like, to facilitate turning of the magnet and its removal from the mounting ring 64.

In another embodiment, the engagement surface of the magnet may be held in place within the mounting by friction fit. As described in more detail below, the outer surface of the magnet, or casing of the magnet, can be shaped in a specific configuration, allowing for insertion of the magnet or part of the magnet into the mounting element. In this regard, the complementary engagement surface of the mounting will be compatible with the shape of the outer surface of the magnet or magnet casing such that the outer surface can be inserted into the mounting element. Once the outer surface of the magnet or magnet casing has been at least partially inserted into the mounting element, the magnet or magnet casing may be rotated, for example a ¼ or ½ turn, thereby causing the shape of the engagement surface of the magnet or magnet casing to no longer be compatible with the shape of the complementary engagement surface of the mounting element. This thereby provides an interference fit preventing inadvertent removal of the magnet from the mounting element. In this embodiment, the magnet may be easily removed by merely rotating the magnet the appropriate amount such that the shape of the engagement surface of the magnet means is compatible with the shape of the complementary engagement surface of the mounting element, thereby allowing easy removal of the magnet.

Figure 3A:
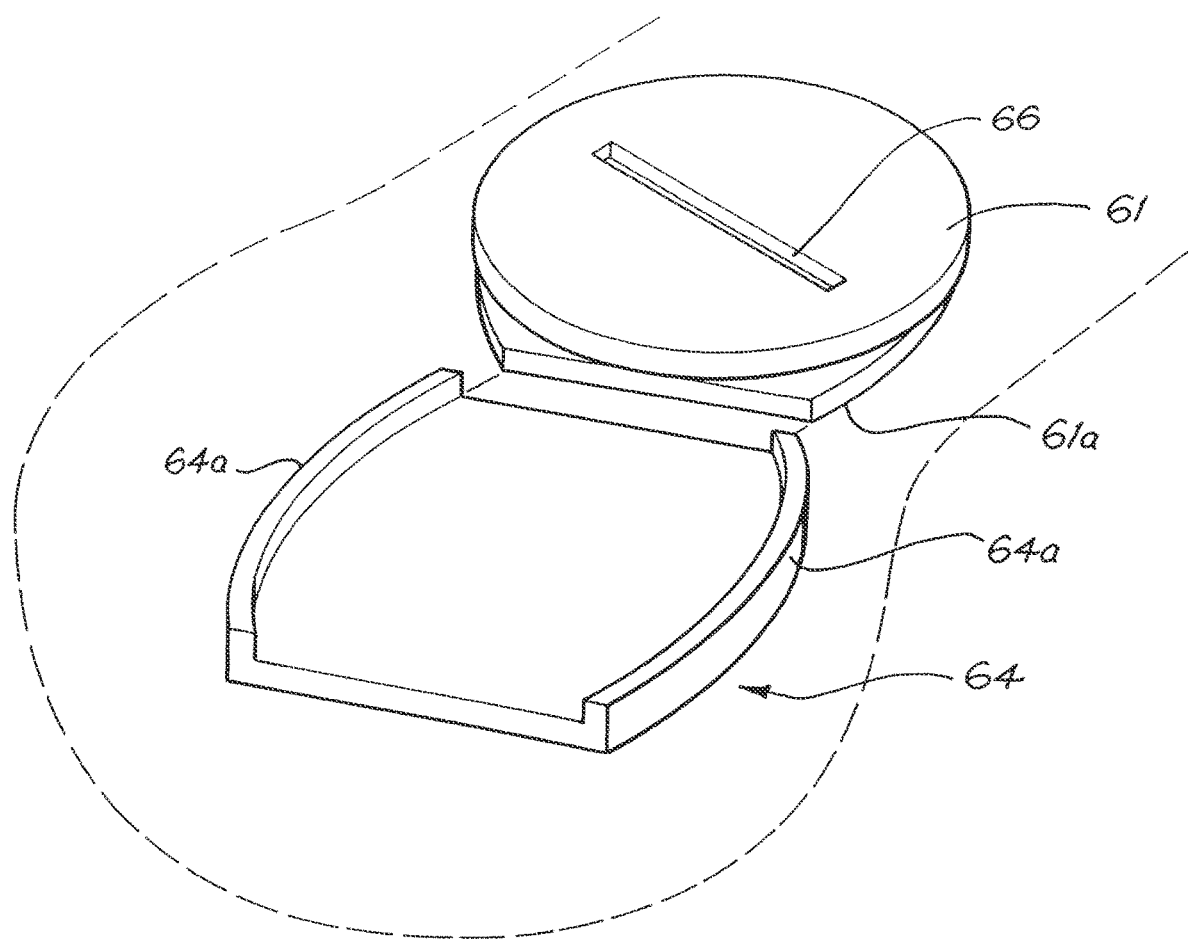
FIGS. 3a and 3b depict a still further arrangement for mounting the magnet in the receiver component.

This particular embodiment is depicted in FIG. 3a wherein magnet 61 is provided with a pedestal element 61a for securing within the mounting element 64. In the depicted embodiment, the mounting element 64, is substantially trapezoidal in shape with two upright walls 64a, being curved in configuration. The pedestal element 61a of the magnet 61 has a similar shape to that of the mounting element 64, namely it has a shape consisting of two substantially parallel sides joined at both ends by curved portions. The pedestal is remote from the bottom face of the magnet 61, thereby forming a space between the pedestal element 61a and the magnet 61. The inner surfaces of the upright walls 64a of the mounting element 64 can be provided with a recess to receive the curved end portions of the pedestal element 61a when the pedestal is placed within the mounting element 64 for engagement.

Figure 3B:
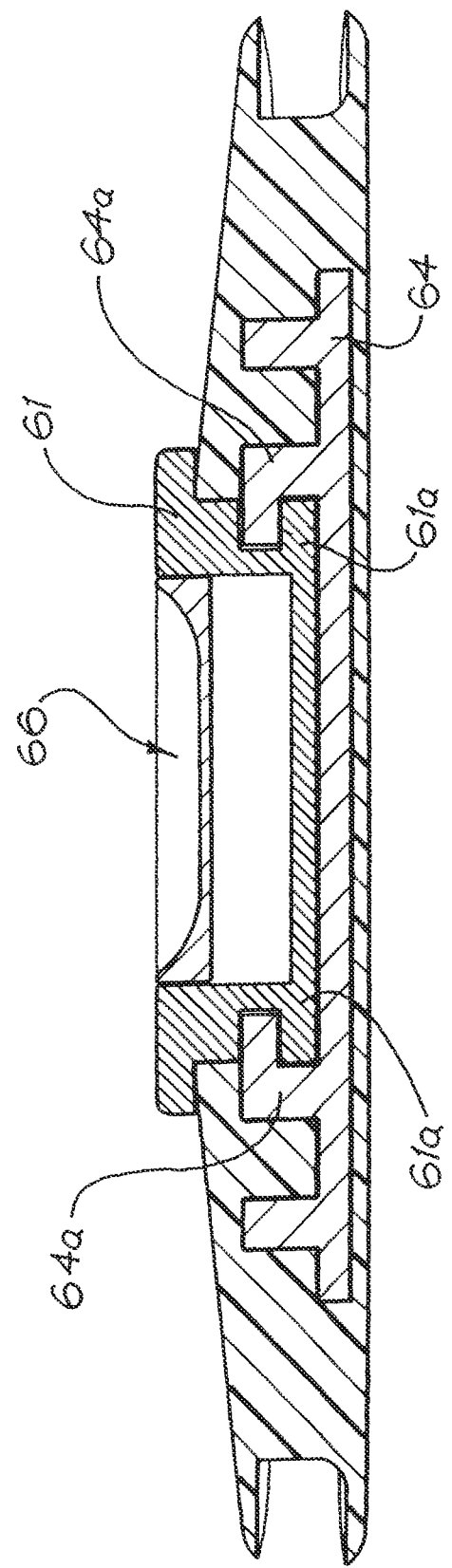

In this regard, the magnet 61 is rotatable relative to the mounting. The magnet may be rotated 90 degrees to the position shown in FIG. 3a for locating within the mounting element 64. Once the magnet 61 is placed in position with the pedestal element 61a located between the walls 64a of the mounting element 64, the magnet is then rotated 90 degrees such that the curved walls of the pedestal element 61a are received within the recessed curved walls of the mounting element 64. In this regard, the magnet is secured in place and is fixed within the mounting element 64 as shown in FIG. 3b. To remove the magnet 61 from the mounting element 64 in the event, for example, of an MRI procedure, the magnet 61 is rotated such that the pedestal element 61a is no longer held in place within the walls 64a of the mounting element. The magnet can then be relatively easily removed. A screwdriver or other such tool can be used to assist in this procedure, via the slot 66.

As is shown in FIGS. 3a and 3b as the dotted line and the hashed area respectively, the magnet 61 and mounting element 64 are preferably secured in a flexible biocompatible material such as silicone. In this regard, the silicone can be arranged so as to overlap the walls of the mounting element 64 such that when the magnet 61 is placed in position for securing, as described above, the surrounding material may be compressed between the magnet 61 and the mounting element 64. In this regard, the compression force may aid in securing the magnet in place when rotated into the secured position. Further, such an arrangement may further seal the arrangement form the ingress of body fluids into the mounting element 64.

In another embodiment, a spring-type force can be provided to aid in the interference fit by providing a bias force between the engagement surfaces of the magnet and the mounting element, such that when the two surfaces are in non-alignment, the magnet will be securely held in place. Such a biasing force can be provided by placing a spring means or spring member in the mounting for receiving the magnet, or by providing a compressive material such as silicone within the mounting, that is compressed once the magnet is inserted into the mounting and provides a force that biases the magnet against the mounting.

Figure 4:
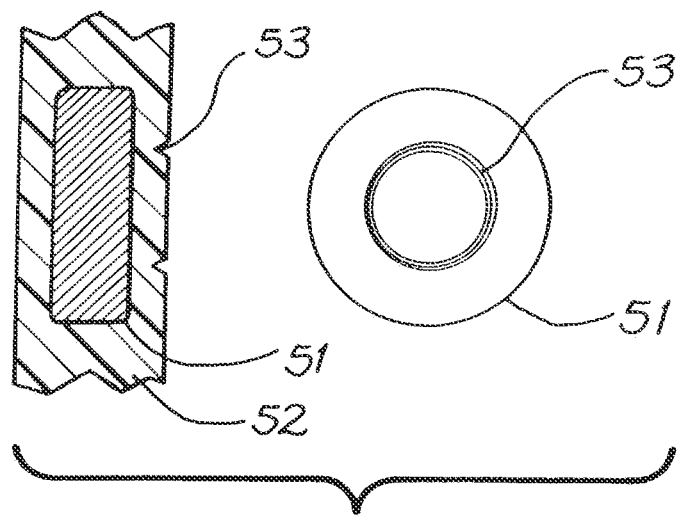
FIGS. 4, 4a and 4b depict arrangements for identifying the location of the magnet in the mounting of the receiver component.
Figure 4A:
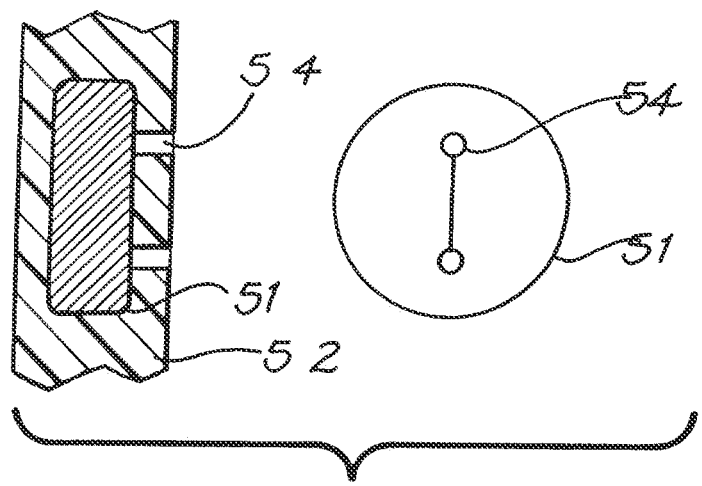
Figure 4B:
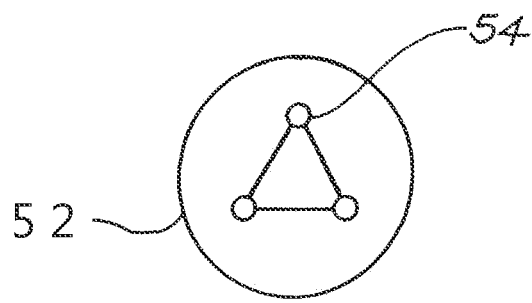

A further aspect of the invention is depicted in FIGS. 4, 4a and 4b. The magnet (here depicted as 51) of the implantable receiver component is housed within a suitable biocompatible flexible silicone mounting 52. In FIG. 4, the mounting 52 has a circular indentation 53 formed therein that acts as an indicia and serves to assist in identifying the location of the magnet 51 within the mounting 52. During surgery to remove the magnet 51, the ring 53 will indicate to the surgeon the location of the magnet 51 within the mounting 52. The indentation can also serve as a guide to a scalpel blade used to cut through the mounting 52 to access the magnet 51.

In the embodiment depicted in FIGS. 4*a* and 4*b*, the indicia can comprise two or more holes 54 formed in the silicone. The holes 54 again act as guides to a surgeon having to cut the magnet 51 from the mounting 52. That is, they identify where the mounting 52 should be cut to allow removal of the magnet 51 held therein.

Figure 5B:
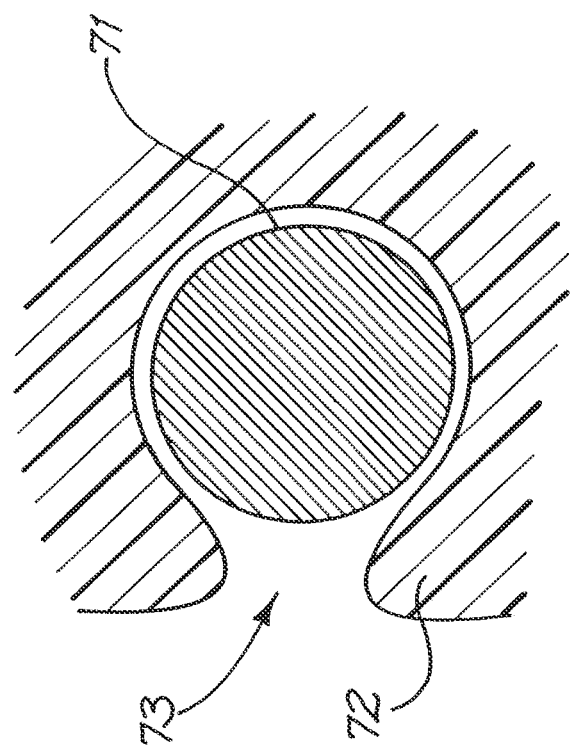
FIGS. 5a and 5b depict an alternative arrangement for mounting the magnet in the receiver component.
Figure 5A:
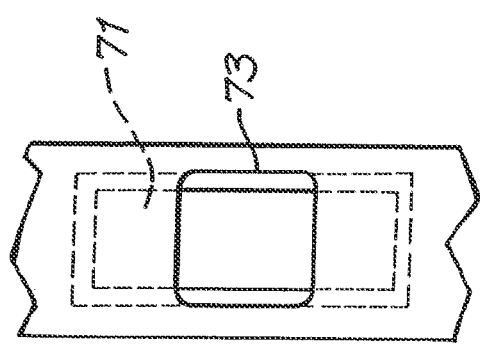

FIGS. 5*a* and 5*b* depict a still further arrangement wherein the magnet 71 of the implantable receiver component is housed within a pocket 72 formed in a wall of the biocompatible flexible mounting. The pocket 72 has a restricted opening 73 formed therein through which the magnet 71 can be inserted but which is sized to retain the magnet 71 within the pocket 72 following insertion during normal use.

Figure 6A:
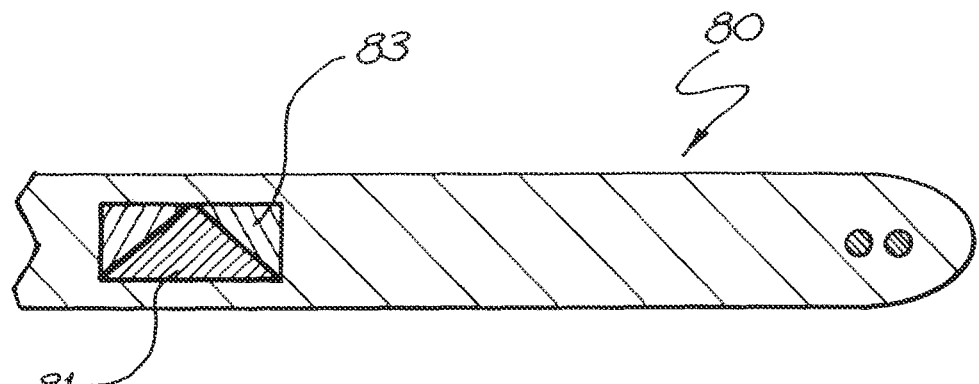
FIGS. 6a and 6b depict another arrangement for ensuring magnetic alignment of the receiver component with the external transmitter component.
Figure 6B:
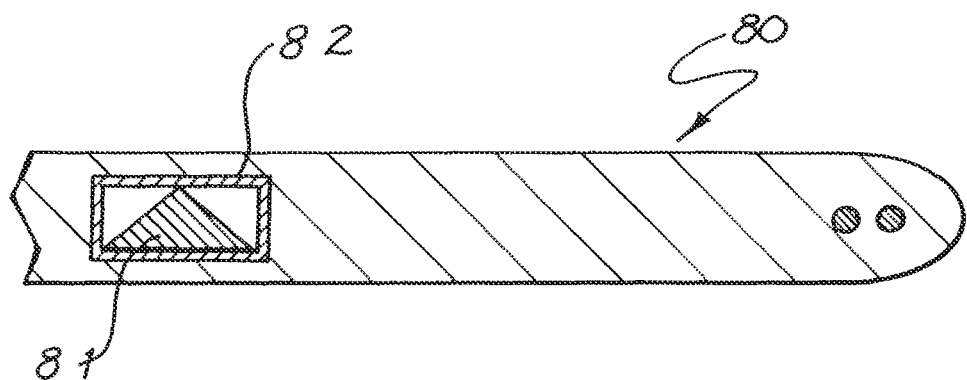

FIGS. 6*a* and 6*b* depict a still further arrangement, in which the external transmitter unit (not depicted in FIGS. 6*a* and 6*b*) has a magnet positioned therein while the implantable receiver component (here depicted as 80) has a conical, non-magnetised ferro-magnetic insert 81 positioned therein to allow transcutaneous alignment of the external transmitter unit and the implantable receiver component. The non-magnetised insert 81 of the implantable receiver component has a first end and a second end and increases in width away from the first end towards the second end, the first end being adapted to be positioned closer to the skin of the implantee to ensure self-centering of the magnet of the external transmitter unit with the insert 81 of the receiver component. While depicted as a conical structure, the magnetised insert be other shapes such as a frusto-conical shape.

The non-magnetised insert 81 can be mounted in a non-magnetic support within the receiver component. In one embodiment, the support can be a titanium case 82 as depicted in FIG. 6*b*. In another embodiment, as depicted in FIG. 6*a*, a suitable non-magnetic material, such as plastic, ceramic or titanium, stop member 83 can lock the insert 81 in the receiver component.

While the insert 81 can be removable, the use of a non-magnetised insert 81 rather than a magnet has the advantage of reducing the magnetic force on the receiver component during an MRI scan if it is left in place.

Figure 7A:
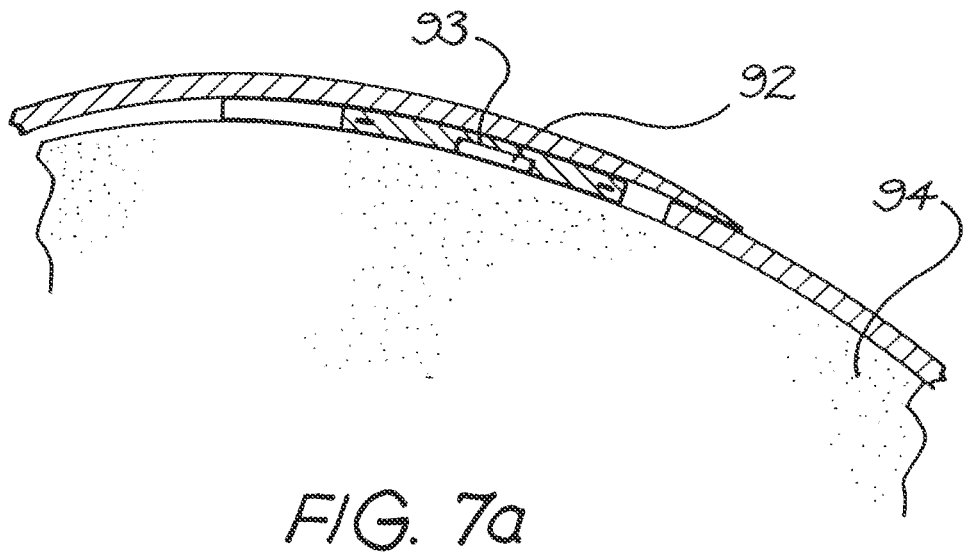
FIG. 7a depicts a further arrangement for mounting the magnet in the receiver component.
Figure 7B:
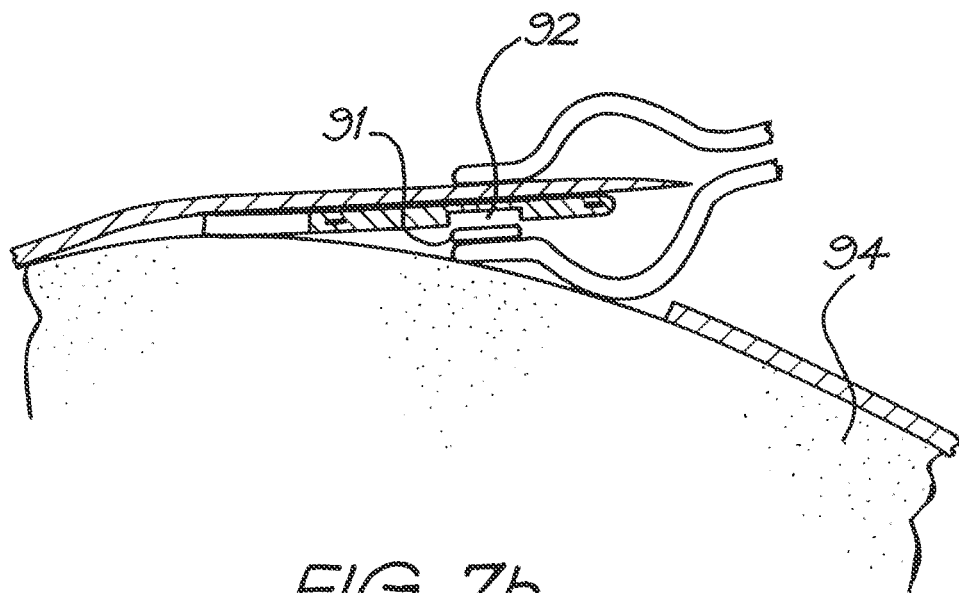

In FIGS. 7*a* and 7*b*, the magnet 91 of the implantable receiver component (here depicted as 92) is housed within a recess 93 formed in a suitable biocompatible flexible mounting. The recess 93 is adapted to be located adjacent the skull 94 of the implantee in use thereby ensuring the magnet 91 is held in the recess 93 between the receiver component 92 and the skull 94 of the implantee.

In this embodiment, the magnet 91 can be removed from the recess by incising the skin of the implantee and then gently lifting the receiver component 92 away from the skull a distance sufficient to allow a surgeon to reach under the receiver component and remove the magnet 91 from the recess 93, as is depicted in FIG. 7*b*.

Figure 8A:
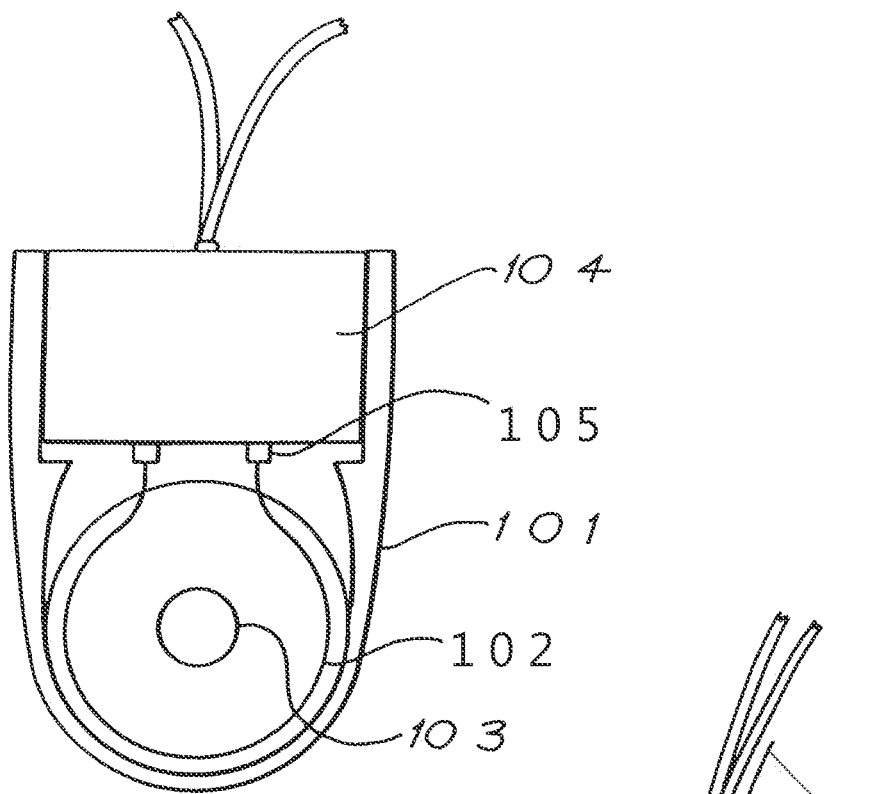
FIGS. 8a and 8b depict an arrangement in which the receiver coil can be disconnected from the stimulator component.
Figure 8B:
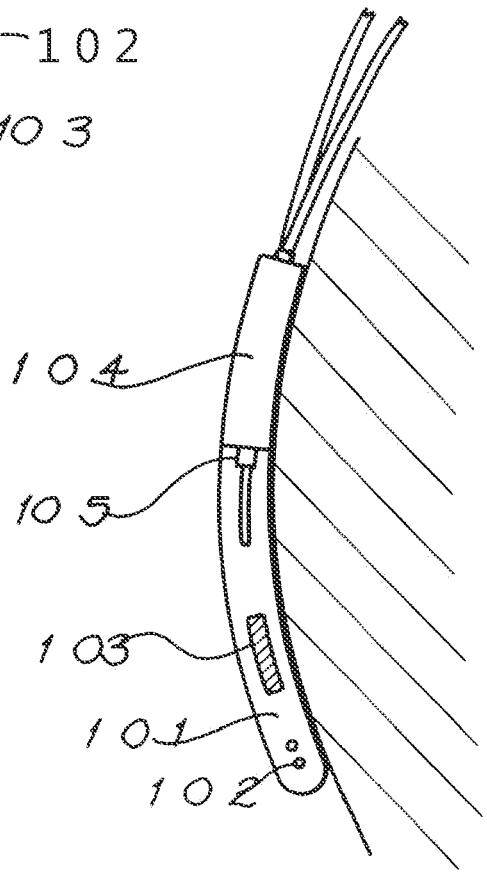

FIGS. 8*a* and 8*b* depict a further arrangement in which the mounting 101 housing the receiver coil 102 and magnet 103 is detachably connectable to an implantable tissue stimulator device (here depicted as 104). Electrical connection is made between the receiver component and the tissue stimulator device when the component is connected to the stimulator device. A pin and socket arrangement can be used to provide the electrical connection.

As depicted, the electrical connection is made between the coil 102 and the circuitry of the tissue stimulator device 104 by a pin and socket arrangement 105. Once connection is made, the pin and socket arrangement is preferably constructed such that there is no ingress of bodily fluids into either the stimulator device 104 or the mounting 101. In one embodiment, the socket can be mounted to the stimulator device and the pin or pins to the receiver component. An arrangement where the socket is part of the receiver component and the pin or pins are part of the stimulator device can be equally envisaged.

If the implantee is to undergo an MRI scan, an incision can be made in the implantee, and the receiver component detached from the tissue stimulator device. The entire receiver component, as defined in this aspect, is then removed rather than just the magnet. Once the MRI scan is complete, the receiver component can be re-implanted and the necessary connection again made between the receiver component and the stimulator device.

Mounting 101 is detachable from the tissue stimulator device 104 and may be removed prior to an MRI procedure. Once the MRI scan is complete, the mounting 101 can be re-implanted and the necessary connection again made between the coil 102 and the stimulator device 104.

In FIGS. 9*a*, 9*b*, 9*c*, 10*a* and 10*b* various systems that rely on one or more clips to removably hold the magnet within the receiver component are depicted.

The clips can be mounted on the receiver component and adapted to engage the magnet positioned therein or thereon. In another embodiment, the clips can be mounted to the magnet or a casing thereof and are engageable with the receiver component. The clips may be manipulable by a surgeon.

Figure 9A:
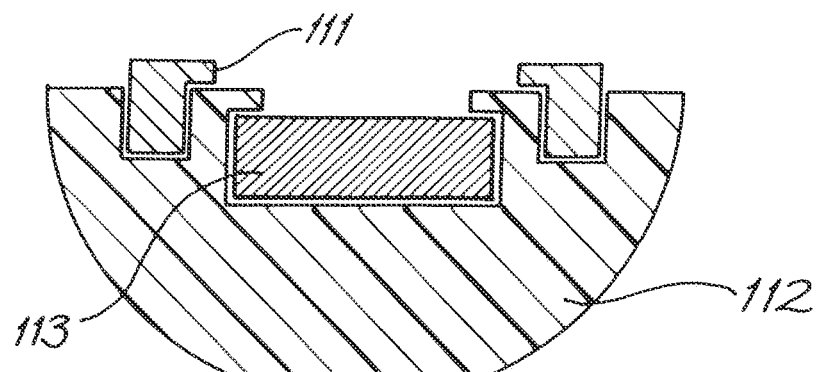
FIGS. 9a, 9b, 9c, 10a, and 10b depict various arrangements for retaining the magnet in the receiver component using one or more manipulable clips.

FIG. 9*a* depicts a compression clip 111 that can be used to compress a silicone pocket 112 around a magnet (here depicted as 113). The clip 111 can be removed by a surgeon if removal of the magnet 113 is required.

Figure 9B:
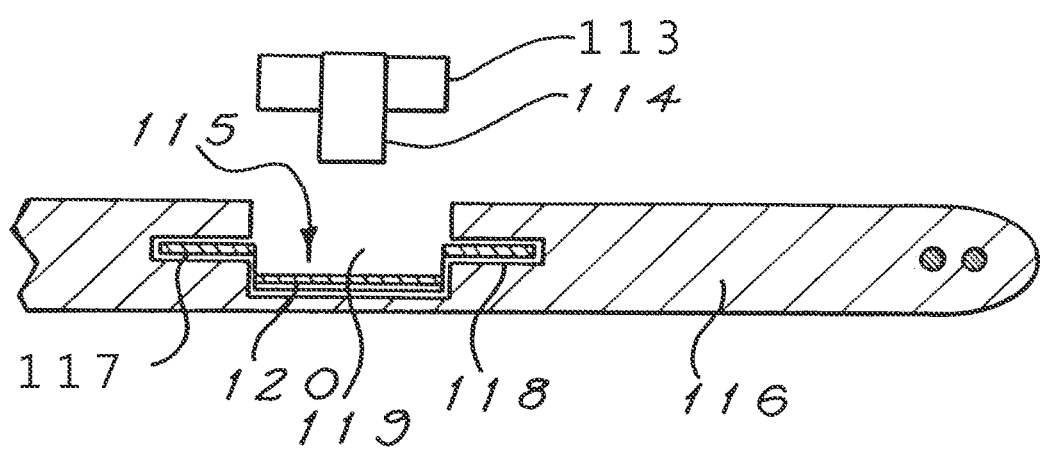
Figure 9C:
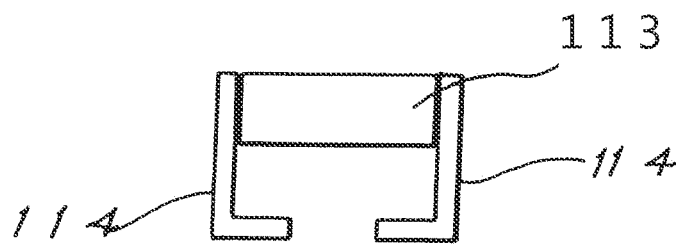

In the embodiment depicted in FIGS. 9*b* and 9*c*, two clips 114 are mounted on the magnet 113 and are engageable with a socket member 115 that is itself removably engageable in the receiver component (here depicted as 116). The socket member 115 has a main member 120 and two wing members 117. The wing members 117 are engageable within recesses 118 extending laterally from a main recess 119 formed in the receiver component 116. When the socket member 115 is positioned within the main recess 119 and the wing members 117 are engaged with the lateral recesses 118, the main member 120 is suspended across the main recess 119.

The clips 114 of the magnet 113 are preferentially biased inwardly and as such must be moved out and around the main member 120 on insertion. Once the lower ends of the clips 114 have moved relatively below the main member 120, the clips 114 can be released and so engage under the main member 120. If it is desired to remove the magnet 113, the clips 114 are pulled relatively apart by the surgeon thereby allowing the magnet 113 to be drawn up and out of the main recess 119.

Figure 10A:
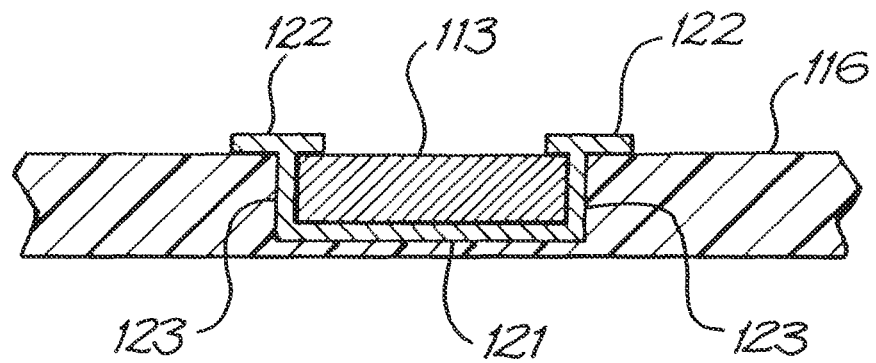
Figure 10B:
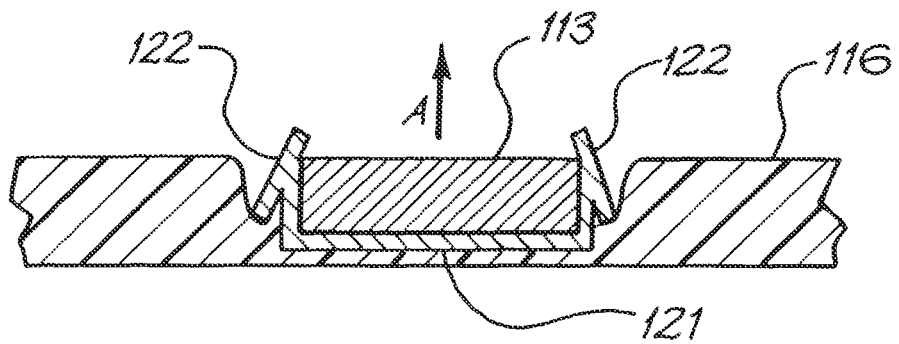

An alternative arrangement for using a clip to retain the magnet 113 in the receiver component 116 is depicted in FIGS. 10*a* and 10*b*. In this embodiment, a clip 121 is positioned underneath the magnet 113. The clip 121 is supported in the silicone body of the receiver component and has two lips 122 that preferentially hold the magnet 113 in place during normal use. If it is desired to remove the magnet 113, the lips 122 are pushed down into the resilient silicone body 116 and pivot about uprights 123 so allowing the magnet 113 to be popped out of the receiver component 116 in the direction of arrow A.

The cochlear implant system described above enables an implantee to undergo an MRI procedure without removing the magnet of an implant, such as a cochlear implant, or provides a system enabling easy removal of the magnet to facilitate an MRI procedure at relatively higher filed strengths. Such a system is particularly useful for those implantees requiring regular MRI scans.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An MRI-compatible implantable receiver component of a cochlear implant comprising:
   a magnet apparatus that includes a casing and a magnet within the casing; and
   a mounting element comprising a central cavity, wherein the mounting element comprises a material selected from the group consisting of:
      a biocompatible metal;
      a biocompatible plastic; and
      a biocompatible ceramic,
   wherein
      the magnet apparatus is releasably held within the mounting element via a compressive material that is configured to be compressed when the magnet apparatus is inserted into the central cavity of the mounting element,
      the magnet apparatus comprises a recessed portion formed in the outer wall of the casing,
      an extension extends inwardly into the central cavity, the extension comprising the compressive material, and
      the compressive material provides a biasing force against the surface of the magnet apparatus to form an interference fit.

2. The MRI-compatible implantable receiver component of a cochlear implant of claim 1, wherein:
   the compressive material is placed adjacent to the recessed portion in the outer wall of the casing.

3. The MRI-compatible implantable receiver component of a cochlear implant of claim 2, wherein:
   the compressive material comprises silicone.

4. The MRI-compatible implantable receiver component of a cochlear implant of claim 2, further comprising:
   an antenna coil encircling the magnet apparatus and mounting element, wherein the antenna coil is adapted to receive coded signals that are transcutaneously transmitted from an external antenna;
   a stimulator unit connected to the antenna coil, wherein the stimulator unit is adapted to process coded signals received by the antenna coil and provide a stimulation signal to an intracochlear electrode assembly; and
   a biocompatible silicone covering at least a portion of the receiver component, the antenna coil, and the stimulator unit.

5. An MRI-compatible implantable receiver component of a cochlear implant comprising:
   a magnet apparatus that includes a casing and a magnet within the casing; and
   a mounting element comprising a central cavity, wherein the mounting element comprises a material selected from the group consisting of:
      a biocompatible metal;
      a biocompatible plastic; and
      a biocompatible ceramic,
   wherein
      the magnet apparatus is releasably held within the mounting element via a compressive material that is configured to be compressed when the magnet apparatus is inserted into the central cavity of the mounting element, and
      the magnet apparatus comprises an engagement surface engageable with a complementary surface to allow for removal of the magnet apparatus, wherein the engagement surface comprises at least one tool interface surface configured to provide a reaction surface for a tool to facilitate removal of the magnet apparatus from the mounting element.

6. The MRI-compatible implantable receiver component of a cochlear implant of claim 5, wherein:
   the implantable receiver component is configured to permit removal of the magnet apparatus by moving the magnet apparatus in a direction that is parallel a cylindrical axis of the magnet apparatus.

7. The MRI-compatible implantable receiver component of a cochlear implant of claim 5, wherein:
   the magnet includes a longitudinal axis and a circular outer periphery extending about the longitudinal axis, wherein the implantable component is configured to permit the magnet to rotate about the longitudinal axis, but otherwise restrain its rotational movement.

8. The MRI-compatible implantable receiver component of a cochlear implant of claim 7, wherein:
   the magnet is rotatable within the casing of the magnet apparatus.

9. An MRI-compatible implantable receiver component of a cochlear implant comprising:
   a magnet apparatus comprising a cylindrical casing having a cylindrical axis and a magnet housed within the casing;
   a mounting apparatus comprising a central cavity adapted to receive and restrain movement of the magnet apparatus in a direction parallel to a longitudinal axis of the central cavity, the mounting apparatus comprising a material selected from the group consisting of:
      a biocompatible metal;
      a biocompatible plastic; and a biocompatible ceramic; and
   a silicone overmoulding that is adapted to encapsulate at least part of the mounting apparatus, wherein
      the silicone overmoulding forms a pocket surrounding the central cavity, wherein the pocket is adapted to receive the magnet apparatus, and
      the magnet apparatus is releasably held within the central cavity of the mounting apparatus by a frictional fit against the silicone overmoulding.

10. The MRI-compatible implantable receiver component of claim 9, wherein:
    the mounting apparatus comprises a mounting plate that is positioned perpendicular to the cylindrical axis of the magnet apparatus, wherein the mounting plate comprises a plurality of holes extending therethrough, wherein the silicone overmoulding passes through the plurality of holes to secure the mounting apparatus to the silicone overmoulding.

11. The MRI-compatible implantable receiver component of claim 9, wherein:
    the silicone overmoulding further comprises a restricted opening through which the magnet apparatus can be inserted into the central cavity, wherein the restricted opening retains the magnet apparatus in the central cavity.

12. The MRI-compatible implantable receiver component of claim 11, wherein:
the implantable receiver component is configured so that the magnet apparatus can be removed from the pocket in the implantable receiver component by pulling the magnet apparatus through the restricted opening.

13. The MRI-compatible implantable receiver component of claim 12, wherein:
removing the magnet apparatus is done by pulling the magnet apparatus in a direction that is perpendicular to the cylindrical axis of the casing of the magnet apparatus.

14. The MRI-compatible implantable receiver component of claim 11, wherein:
the restricted opening forms a seal with the magnet apparatus to prevent the ingress of body fluids into the central cavity.

15. The MRI-compatible implantable receiver component of claim 9, wherein:
the magnet apparatus further comprises a tab that protrudes outwardly from the cylindrical casing; and
the tab forms a friction fit with the silicone overmoulding when the magnet apparatus is inserted into the central cavity of the mounting apparatus to seal the central cavity to prevent ingress of body fluids into the central cavity.

16. The MRI-compatible implantable receiver component of claim 9, wherein:
the casing of the magnet apparatus is configured to permit the magnet to rotate about the cylindrical axis, but otherwise restrain its rotational movement.

17. The MRI-compatible implantable receiver component of claim 16, wherein:
the casing of the magnet apparatus comprises a spacing between inner walls of the casing and the magnet to permit the magnet to rotate within the casing of the magnet apparatus.

18. The MRI-compatible implantable receiver component of claim 17, further comprising:
an antenna coil encircling the magnet apparatus and mounting apparatus, wherein the antenna coil is encapsulated within the silicone overmoulding and is adapted to receive coded signals that are transcutaneously transmitted from an external antenna; and
a stimulator unit connected to the antenna coil, wherein the stimulator unit is adapted to process coded signals received by the antenna coil and provide a stimulation signal to an intracochlear electrode assembly.

19. The MRI-compatible implantable receiver component of claim 9, wherein:
the implantable receiver component is configured so that the magnet apparatus can be removed from the implantable component after the implantable receiver component has been implanted into a patient.

20. An MRI-compatible implantable receiver component of a cochlear implant comprising:
a magnet apparatus that includes a casing and a magnet within the casing; and
a mounting element comprising a central cavity, wherein the mounting element comprises a material selected from the group consisting of:
a biocompatible metal;
a biocompatible plastic; and
a biocompatible ceramic,
wherein
the magnet apparatus is releasably held within the mounting element via a compressive material that is configured to be compressed when the magnet apparatus is inserted into the central cavity of the mounting element,
the magnet apparatus comprises a recessed portion formed in the outer wall of the casing,
the mounting element comprises an extension that extends inwardly into the central cavity, and
the compressive material provides a biasing force against the surface of the magnet apparatus to form an interference fit.

21. The MM-compatible implantable receiver component of a cochlear implant of claim 20, wherein:
the compressive material is placed adjacent to the recessed portion in the outer wall of the casing.

22. The MM-compatible implantable receiver component of a cochlear implant of claim 20, wherein:
the compressive material comprises silicone.

23. The MM-compatible implantable receiver component of a cochlear implant of claim 20, further comprising:
an antenna coil encircling the magnet apparatus and mounting element, wherein the antenna coil is adapted to receive coded signals that are transcutaneously transmitted from an external antenna;
a stimulator unit connected to the antenna coil, wherein the stimulator unit is adapted to process coded signals received by the antenna coil and provide a stimulation signal to an intracochlear electrode assembly; and
a biocompatible silicone covering at least a portion of the receiver component, the antenna coil, and the stimulator unit.

* * * * *